United States Patent
Forestiere et al.

(10) Patent No.: US 6,486,362 B1
(45) Date of Patent: Nov. 26, 2002

(54) PROCESS FOR PRODUCING OXYGEN-CONTAINING COMPOUNDS CONTAINING AT LEAST ONE OXYGEN ATOM BONDED TO TWO DISTINCT CARBON ATOMS WHICH ARE NOT BONDED TOGETHER AND NOT INCLUDING A MULTIPLE BOND

(75) Inventors: Alain Forestiere, Vernaison (FR); Jean-Ferdinand Gaillard, Lyons (FR); Michel Barraque, Le Pecq (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/606,018

(22) Filed: Jun. 29, 2000

(30) Foreign Application Priority Data

Jun. 26, 1999 (FR) .............................. 99 08443

(51) Int. Cl.$^7$ .............................. C07C 41/00; C10L 1/18
(52) U.S. Cl. .................. 568/698; 568/591; 568/594; 568/605; 568/671; 44/444; 44/447
(58) Field of Search .................. 44/444, 447; 568/695, 568/698, 671, 591, 594, 605

(56) References Cited

U.S. PATENT DOCUMENTS

| | | | | |
|---|---|---|---|---|
| 4,390,734 A | * | 6/1983 | Knifton | 568/678 |
| 4,426,541 A | * | 1/1984 | King | 568/881 |
| 4,579,979 A | * | 4/1986 | Andrade et al. | 568/596 |
| 5,446,208 A | * | 8/1995 | Koshino et al. | 568/670 |
| 5,520,710 A | | 5/1996 | Olah | 44/447 |
| 6,013,114 A | * | 1/2000 | Hille et al. | 44/444 |

FOREIGN PATENT DOCUMENTS

| | | |
|---|---|---|
| EP | 0 855 436 A2 | 7/1998 |
| FR | 1.253.998 | 5/1961 |
| GB | 749315 | 5/1956 |
| GB | 2 323 844 A | 10/1998 |
| JP | 53132514 A * | 11/1978 |
| WO | WO 94/26685 | 11/1994 |

* cited by examiner

Primary Examiner—Margaret Medley
(74) Attorney, Agent, or Firm—Millen, White, Zelano & Branigan, P.C.

(57) ABSTRACT

A process for producing oxygen-containing compounds containing at least one oxygen atom bonded to two distinct carbon atoms which are not bonded together and not comprising a multiple bond comprises a step a) for hydroformylation of a feed comprising at least one olefin containing four to seven carbon atoms to at least one aldehyde, in the presence of a catalyst and a synthesis gas under hydroformylation conditions, a step b) for hydrogenation of this aldehyde to at least one corresponding alcohol, and a step c) for transforming at least one alcohol obtained from step b) in the presence of a catalyst under conditions for producing a mixture containing at least one ether or at least one acetal.

15 Claims, No Drawings

PROCESS FOR PRODUCING OXYGEN-CONTAINING COMPOUNDS CONTAINING AT LEAST ONE OXYGEN ATOM BONDED TO TWO DISTINCT CARBON ATOMS WHICH ARE NOT BONDED TOGETHER AND NOT INCLUDING A MULTIPLE BOND

The invention relates to a process for producing oxygen-containing compounds containing at least one oxygen atom bonded to two distinct carbon atoms which are not bonded together and not comprising a multiple bond. This oxygen-containing compound belongs to the group formed by ethers or to the acetal group.

The production of ether from a hydrocarbon feed containing olefins has been described, for example, in International patent WO-A-94/26685. That document describes the production of a mixture of ether and alcohol by hydrating a feed comprising an olefin containing two to eight atoms in the presence of a catalyst comprising a modified beta zeolite. The examples are limited to the case of forming isopropyl alcohol and diisopropylether from propylene.

U.S. Pat. No. 886,918 describes a process for producing ether(s) of a mixture of ether(s) and alcohol(s) from a feed comprising at least one olefin containing two to seven carbon atoms, introduced into two reaction zones of a conversion unit. The first zone consists of hydrating the olefin to the alcohol. In the second zone, a portion of the lipido-colloid is dehydrated to the ether and a further portion of that alcohol reacts with the olefin introduced into that zone to form the ether. The catalysts used in the hydration and etherification zones contain identical or different acidic zeolites. That process only describes the case where the olefin is propylene.

French patent FR-A-1 576 890 describes a process for preparing acetals by reacting an alcohol containing three to eight carbon atoms and aldehyde generating substances such as trioxane, in the presence of acidic catalysts such as ion exchange resins.

The process of the invention is of particular application to feeds containing linear or branched olefins containing four to seven carbon atoms in their molecule and produced by conventional manufacturing routes such as fluid catalytic cracking (FCC), steam cracking, oligomerisation of olefins containing less than four carbon atoms, or by dimerisation of olefins containing less than four carbon atoms using, for example, the DIMERSOL process from the Institut Francais du Pétrole.

By way of example, gasolines from catalytic cracking units enable different hydrocarbon cuts with a high olefin content to be produced. In future, gasolines used as fuels must contain fewer olefins for environmental reasons. Further, ethers and acetals have high cetane numbers in mixtures. Firstly, the process of the invention can eliminate olefinic FCC gasolines and secondly, it can convert them into ethers or acetals which when added in suitable proportions to gas oils result in a gas oil with a cetane number which is higher than that of the starting gas oil. Further, incorporating these oxygen-containing compounds into the gas oil can produce a gas oil which pollutes less. The invention thus concerns a process for upgrading these olefinic cuts and in particular olefinic cuts from FCC which can also improve gas oil oils obtained in the refinery either by distillation or by transformation of other cuts, for example the gas oil cut from FCC. The invention also concerns a gas oil with an improved cetane number obtained by incorporating at least one oxygen-containing product formed in the process of the present invention. It further concerns the use of these products, ethers and/or acetals and in particular ethers as bases for high cetane number fuels.

In a particular implementation of the invention, the olefins contain five to six carbon atoms and originate from a light gasoline cut leaving a FCC unit. This particular implementation of the invention is better for simultaneous upgrading of both the gasoline cut obtained by cracking by eliminating a large fraction of the olefins it contains to produce a gasoline cut with a lower olefin content, and of the gas oil obtained by cracking by adding at least a portion of the oxygen-containing compounds formed during elimination of the olefins from the gas cut, resulting in the production of a gas oil fuel with a cetane number which is higher than that of the cracked gas oil without additives.

The process of the present invention for producing oxygen-containing compounds containing at least one oxygen atom bonded to two distinct carbon atoms which are not bonded together and not comprising a multiple bond comprises a step a) for hydroformylation of a feed comprising at least one olefin containing four to seven carbon atoms to at least one aldehyde, a step b) for hydrogenating this aldehyde to at least one corresponding alcohol, and a step c) for transforming at least one alcohol obtained from step b) into a mixture of products comprising at least one oxygen-containing compound containing at least one oxygen atom bonded to two distinct carbon atoms which are not bonded together and not comprising a multiple bond. This product mixture comprises at least one oxygen-containing compound containing at least one oxygen atom bonded to two distinct carbon atoms which are not bonded together and not comprising a multiple bond belonging to the ether or to the acetal group.

Step a) of the process of the invention comprises hydroformylation of a feed comprising at least one olefin containing four to seven carbon atoms in its molecule. Hydroformylation transforms the feed containing at least one olefin into at least one aldehyde containing five to eight carbon atoms in its molecule. It is carried out in the presence of a hydroformylation catalyst and a synthesis gas comprising a mixture of carbon monoxide and hydrogen in a $H_2/CO$ ratio in the range about 0.5:1 to 3:1, normally in the range about 1:1 to 2.3:1 and usually in the range 1.5:1 to 2.3:1.

The hydroformylation process used in the context of the present invention is preferably the KUHLMANN (PCUK) process described in "Reactivity and Structure Concepts in Organic Chemistry", 1980, volume 1, published by Springer-Verlag, Berlin, Heidelberg, N-Y, pp 165–166.

The catalyst used can be any hydroformylation type catalyst based on cobalt, rhodium or ruthenium. Usually, catalysts based on cobalt or rhodium in the form of carbonyls or carbonyl complexes are used. Preferably, a catalyst based on unmodified carbonyl cobalt is used which has the advantage of being less sensitive than rhodium based catalysts to poisons such as acetylenic compounds, sulphur, halogens, and carboxylic acids. In a particular implementation of the process of the invention, the hydroformylation catalyst used in step a) is dicobalt octacarbonyl $Co_2(CO)_8$.

Hydroformylation uses a mixture of carbon monoxide and hydrogen known as synthesis gas obtained using any method which is known to the skilled person. In particular, said synthesis gas is obtained by partial oxidation of straight run vacuum residues. Synthesis gas normally contains five principal elements, namely hydrogen, carbon monoxide, carbon dioxide, methane and water, and also impurities which originate from the feeds being treated or from the oxygen used, such as argon, nitrogen and hydrogen sulphide.

Manufacturing synthesis gas by partial oxidation usually involves distilling air to obtain a gaseous mixture which is highly enriched in oxygen containing, for example, 95% by volume of oxygen. The petroleum residue is then partially oxidised using this highly oxygen-rich gaseous mixture. The high temperature encourages the formation of soot which can be limited by injecting water vapour.

The gaseous mixture obtained is then enriched in hydrogen by steam converting carbon monoxide which can be encouraged by an excess of steam. After cooling by quenching, the synthesis gas is separated from the acidic gases such as carbon dioxide and hydrogen sulphide using any means which is known to the skilled person such as adsorbing the acidic compounds onto a capture mass or in a basic solution.

Hydroformylation is carried out in a reactor in the liquid phase. The temperature is normally in the range about 100° C. to 200° C., usually in the range about 150° C. to 180° C., and the total pressure is normally in the range about 10 to 50 MPa, usually in the range about 20 to 40 NPa, and more preferably in the range about 25 to 30 MPa.

The hydroformylation reaction generates aldehydes and primary alcohols as the principal products, in particular when the $H_2/CO$ ratio is 1.5:1 or more. The product obtained following hydroformylation contains paraffins and secondary products such as heavier compounds, for example the trimer and tetramer of the olefins.

Only the aldehyde and alcohol stream, which is separated using any means known to the skilled person, is sent to the hydrogenation unit. The paraffins originating from the FCC and the secondary products are evacuated.

Step b) of the process of the invention is hydrogenation to at least one primary alcohol of at least one aldehyde obtained in step a). Hydrogenation of aldehydes to the corresponding primary alcohols is known in the art. It can be carried out in the liquid phase or in the gas phase. The article in "Hydrocarbon Processing" of March 1993, pages 67–74 describes different aldehyde hydrogenation catalysts such as catalysts based on cobalt, nickel and/or copper with the recommended addition of an alkali element and/or a transition metal, on a silicon oxide support. Copper and nickel are highly sensitive to sulphur and phosphorous compounds, and thus the use of catalysts operating at high temperatures and pressures but which are less sensitive to these impurities has been proposed. Non limiting examples which can be cited are a catalyst based on oxides of zinc and chromium with or without an aluminium oxide, the catalyst based on molybdenum disulphide on carbon, and the catalyst $NiS/WS_2$.

In one particular implementation of the process of the invention, hydrogenation is carried out in the liquid phase and in two steps. The first step is carried out in the presence of a catalyst which is preferably based on molybdenum disulphide on carbon and the second step is carried out in the presence of a catalyst which is normally different from that used in the first step. In this second step the catalyst used is preferably based on nickel on alumina. The reaction temperature is normally in the range about 100° C. to 300° C., usually in the range about 200° C. to 250° C., and the partial pressure of hydrogen is normally in the range about 10 to 30 MPa, usually in the range 15 to 25 MPa. The operating conditions are usually identical in the two steps. The hydrogenated product is usually treated using any means known to the skilled person to produce a fraction which is enriched in alcohol which is used in step c) of the process of the invention to form a mixture of products containing at least one ether or at least one acetal.

In the case of ether production, step c) of the process of the invention is dehydration of at least two molecules of alcohols obtained in step b). The mixture of products obtained during this dehydration comprises at least one ether containing 10 to 16 carbon atoms in its molecule, and usually 12 to 14 carbon atoms in its molecule, unconverted alcohol, olefins and water. The ether obtained can be symmetrical or unsymmetrical.

The catalyst used in the dehydration reaction is any type of catalyst which is well known to the skilled person to carry out this reaction. Preferably, an acidic catalyst usually comprising at least one solid mineral, for example a polysiloxane, grafted with at least one organic alkyl sulphonic acid type group normally containing 1 to 24 carbon atoms, preferably 2 to 20 carbon atoms and more preferably 2 to 5 carbon atoms in the alkyl group, or an aryl sulphonic group normally containing 6 to 18 carbon atoms in the aryl group, or an alkylaryl sulphonic group normally containing 7 to 24 carbon atoms in the alkylaryl group.

In particular, said catalyst, which preferably comprises a polysiloxane type solid grafted with at least one organic group, is sold by DEGUSSA under the registered trade mark "DELOXAN". The preparation of such a solid is, for example, described in U.S. Pat. Nos. 4,552,700, 5,354,831 and 5,380,791. These solids have a strong Bronsted acidity.

The polysiloxane type solid mineral used is preferably grafted with at least one alkylsulphonic acid type organic group. This mineral solid in the catalyst used in step a) of the process of the invention generally comprises at least one unit with formula (I) below:

$$(O_{3/2}Si-R^1-SO_3^-)H^+ \qquad (I)$$

where $R^1$ is an alkyl radical usually containing the number of carbon atoms mentioned above.

These catalysts can operate at low temperature, for example at 130° C., which encourages good catalyst stability, and which also means a long catalyst service life. If the endothermic nature of the reaction is also taken into account, and thus the favourable displacement of the thermodynamic equilibrium by raising the temperature, with these catalysts it is possible to operate at a high temperature (typically between 180° C. and 220° C.).

The fact that the grafted solid is mineral and non organic, for example polysiloxane in type, means that such temperatures can be used without substantial degradation of the catalyst.

The primary alcohols obtained in step b) are dehydrated in the liquid phase at a temperature which is normally in the range about 100° C. to 300° C., usually in the range 120° C. to 250° C. and at a pressure which is normally in the range about 0.1 to 0.3 MPa. The mixture of products formed during this endothermic reaction contains ethers as the principal products and olefins as the secondary products, also unconverted alcohols and water.

This mixture of products containing at least one ether, at least one olefin, at least one unconverted alcohol and water, is then transferred to the fractionation section from which the desired ethers are recovered. Recycling at least a portion of the olefins contained in this mixture to hydroformylation step a) can be envisaged. Similarly, a portion of the unconverted alcohols obtained in step c) can be isolated form the mixture of products by at least one separation then recycled to the inlet to dehydration step c).

In a particular implementation of the process of the invention, the olefins obtained in step c) are isolated from the mixture using two separation steps, normally a distillation followed by decanting and the unconverted alcohols obtained in step c) are isolated from the mixture, usually by two successive distillation steps.

The olefins and water obtained from step c) are separated from the ethers and unconverted alcohols by distillation at a pressure in the range about 0.1 to 1 MPa, usually in the range 0.2 to 0.6 MPa. The olefins and water leave overhead; the ether and unconverted alcohol leave from the bottom of the column. Said olefin is then separated from the water by decanting.

The ether and unconverted alcohol are also fractionated, usually by distillation, at a pressure in the range about 0.1 to 1 MPa, usually in the range 0.2 to 0.6 MPa. The unconverted alcohol leaves overhead and the ether is removed from the column bottom. The alcohols are usually about 50 to 95 mole % converted to ethers and the unconverted can be recycled to transformation step c).

In the case of acetal production, step c) of the process of the invention is an acetal synthesis which transforms the primary alcohol obtained in step b) into a mixture of products comprising at least one acetal containing 11 to 17 carbon atoms, unconverted alcohol and water. The acetals which are obtained contain 11, 13, 15 or 17 carbon atoms. They can be symmetrical, unsymmetrical, linear and/or branched.

The acetals can be synthesised by reacting the primary alcohol obtained in step b) with 1,3,5-trioxane or with a 1,3,5-trioxane derivative containing at least one alkoyl substituent in the 2, 4 or 6 position in the presence of an acidic catalyst. This reaction is encouraged by the presence of a small quantity of water; it is thus encouraged by recycling unconverted alcohol which contains water. By way of non limiting example, said catalyst can be an acidic ion exchange resin (H$^+$), preferably a sulphonic resin such as AMBERLYST 15 from Röhm & Haas.

The operating conditions are: a temperature normally in the range about 70 ° C. to 100° C., a hourly space velocity (HSV) of about 0.1 to 10 h$^{-1}$, and a pressure normally in the range about 0.2 to 1 MPa, preferably in the range about 0.2 to 0.5 MPa.

1,3,5-trioxane has low solubility in alcohol and tends to re-crystallise when the temperature drops. The acetal formation procedure usually comprises stirring the alcohol-trioxane mixture at a temperature normally in the range about 10 to 100° C., preferably in the range about 40° C. to 60° C., for 1 to 20 hours (h) and normally using a mixture in which the mole ratio between the 1,3,5-trioxane and the alcohols is in the range about 3 to 20, usually in the range about 3 to 15, to completely dissolve the trioxane.

In addition to the acetals formed, the mixture of products obtained in step c) also comprises trioxane and alcohol which has not reacted and essentially heavy products from trioxane ring opening, different from that envisaged for acetal formation.

The acetal obtained in step c) is isolated from the mixture of products by at least one separation step. A portion of the unconverted alcohols obtained in step c) is also isolated from the product mixture by at least one separation step then recycled to acetal synthesis step c).

In a preferred implementation of the process of the invention, said acetal is isolated by two successive distillation stages. The first distillation stage is carried out substantially at atmospheric pressure and at a temperature sufficient to distil the unconverted alcohol and the water formed. Acetal and a distillation residue (polyformol) which is soluble in water, is recovered from the bottom of the column, and the unconverted alcohol and water are recovered overhead. The second distillation stage is carried out under vacuum under reduced pressure, normally in the range about 100 to 500 Pa. Acetal is recovered overhead and the residue is recovered from the bottom of the column.

The water and unconverted alcohol from the first distillation stage are separated using any method which is known to the skilled person. As an example, simple decanting can recover a phase which is rich in alcohols containing a portion of the unconverted alcohols and a little water and which is recycled to acetal synthesis step c), also a phase which is rich in water.

The following examples illustrate the invention without in any way limiting its scope.

EXAMPLE 1

The feed contained olefins from a light gasoline cut leaving an FCC unit and containing 5 to 7 carbon atoms in the molecule. This was termed the C5-C7 feed.

The catalyst used was dicobalt octacarbonyl containing about 0.1% by weight (in the form of cobalt). It was introduced into the reactor in the liquid phase. The temperature was about 165° C. and the pressure was about 27.5 MPa. The reaction involved a H$_2$/CO synthesis gas.

The synthesis gas was obtained by partial oxidation of a vacuum residue from distilling crude oil. 344 grams per hour (g/h) of said residue was partially oxygenated with 95% by volume oxygen then the gas mixture was enriched in hydrogen by steam conversion of the carbon monoxide. The synthesis gas obtained was then cooled by quenching and the acidic gases were separated out. The H$_2$/CO ratio was about 1.9:1.

Secondary reactions generated paraffins and heavy compounds such as olefin trimers and tetramers. The heavy compounds and the paraffins were separated by distillation of the stream of aldehydes and primary alcohols originating from the hydrogenation unit.

Hydrogenation took place in the liquid phase in two steps at a temperature of about 225° C. and at a partial pressure of hydrogen of about 20 MPa. The catalyst used in the first step contained, expressed as the weight of metal, 22.7% of molybdenum disulphide (MoS$_2$) and 0.8% of NiS on a carbon support and that of the second step was a catalyst based on nickel on alumina containing, expressed as the weight of metal, 0.7% of NiO. The effluent obtained was analysed regularly by chromatography.

6 grams (g) of DELOXAN ASP solid catalyst was then introduced into a reactor with the effluent obtained above, at a temperature of about 200° C. and at a pressure of about 0.2 MPa. The mixture of products obtained during this dehydration was distilled at a pressure of about 0.4 MPa to separate firstly water and olefin from the mixture obtained and secondly a fraction containing unconverted alcohol and the ether formed. A second distillation stage carried out at a pressure of about 0.4 MPa fractionated the unconverted alcohol and the ether. The olefin was also separated from water by decanting then recycling to the hydroformylation reactor. A portion of the unconverted alcohols was recycled to the dehydration reactor.

The results of the process of the invention are shown in the tables below:

| Reactants | Inlet (g/h) |
| --- | --- |
| Synthesis gas | 422.4 |
| C5–C6 cut | 2184.3 |
| Hydrogen (substantially pure for hydrogenation) | 23.4 |

-continued

| Total | 2630.1 |
|---|---|

| Products | Outlet (g/h) |
|---|---|
| Ethers | 928.6 |
| Synthesis gas | 42.7 |
| Saturates (products from hydrogenating olefins present in the feed) | 1291.2 |
| Heavy compounds (olefin trimers and tetramers) | 27.3 |
| C6–C7 olefins (linear and branched) | 213.9 |
| Water | 126.4 |
| Total | 2630.1 |

It can be seen that the process of the invention can transform a large portion of the olefins contained in the light gasoline FCC cut. The degree of conversion of alcohols to ethers was 83 mole %.

EXAMPLE 2

The hydroformylation and hydrogenation steps were repeated using a feed containing linear butenes being transformed into a mixture of about 72% of 1-pentanol and 25% of 2-methyl-1-butanol. These alcohols contain five carbon atoms in the molecule. They then reacted over 1,3,5-trioxane to form acetals in the presence of AMBERLYST acidic ion exchange resin. The composition of the alcohol mixture is given in Table 1.

To obtain complete dissolution, 306 g of 1,3,5-trioxane was dissolved in a large excess of a mixture of alcohols, with stirring at 50° C., over 16 hours (h). The alcohol/trioxane mole ratio was about 10.

10 g of AMBERLYST 15 WET resin moistened with 8 cm$^3$ of 1-pentanol was then introduced into a 50 cubic centimeter (cm$^3$) tube reactor. It occupied 24 cm$^3$ and was maintained between two layers of glass beads. The alcohols circulated in upflow mode (from bottom to top in the reactor) and were transported from a 5 liter bottle using a pump. The reactor was provided with a double envelope in which a heat transfer fluid was circulated, connected to a thermostatted bath, to regulate the bath. A thermocouple placed inside a sleeve crossing the reactor from side to side measured the temperature inside the reactor. The pressure was about 0.3 MPa. It was maintained by a pressure regulator. The effluent was analysed by gas chromatography.

The acetals obtained were isolated from the effluent by successive distillations. The first distillation was carried out at ambient temperature and at a temperature of about 137.8° C. The second step was carried out at a temperature of about 118° C. at a pressure of 13 torr (1 torr equals 133.32 Pascals).

TABLE 1

The HSV was 1 h$^{-1}$.

| Products | Composition (wt %) |
|---|---|
| 1,3,5-trioxane | 1.77 |
| Pentanal | 0.07 |
| 3-methyl-1-butanol | 0.07 |
| 2-methyl-1-butanol | 25.75 |
| 1-pentanol | 71.99 |
| Ether | 0.17 |
| Others | 0.18 |

TABLE 1-continued

The HSV was 1 h$^{-1}$.

| Products | Composition (wt %) |
|---|---|
| Total | 100 |
| Water content (parts per million, ppm) | 1900 ppm |

The following results were obtained form acetal synthesis:

| Temperature (° C.) | α$_{(alcohols)}$ | S$_{(acetal)}$ | Yield |
|---|---|---|---|
| 70 | 43.6 | 99.4 | 43.3 |
| 80 | 48.5 | 99.1 | 48.1 |
| 90 | 51.1 | 99.0 | 50.6 |
| 100 | 50.0 | 98.9 | 49.4 |

The alcohol conversion is expressed as:

$$\alpha_{alcohol} = \frac{[alcohol]feed - [alcohol]effluent}{[alcohol]feed}$$

The acetal selectivity is:

$$S_{acetal} = \frac{[acetal]}{[acetal] - [products\text{-}secondaries]}$$

The secondary products are essentially heavy products from trioxane ring opening, different from that envisaged for acetal formation.

From the point of view of selectivity, acetals were the major products.

Under optimum conditions, the yield was 50.6%. Unconverted alcohols were then isolated from the mixture by two successive distillation steps then recycled to the acetal synthesis reactor.

What is claimed is:

1. A process for preparing an oxygen-containing compound containing at least one oxygen atom bonded to two distinct carbon atoms which are not bonded together and not comprising a multiple bond which is from the ether group, said process comprising:

a step a) for catalytic hydroformylation of a feed comprising at least one olefin containing four to seven carbon atoms to at least one aldehyde, a step b) for hydrogenating said aldehyde to at least one corresponding alcohol carried out in the liquid phase in two successive steps, in a first step using a catalyst based on molybdenum disulphide on carbon and in a second step using a catalyst based on nickel on alumina, each of these steps being carried out at a temperature in the range of 100° C. to 300° C. and at a partial pressure of hydrogen in the range of 10 to 30 MPa, and a step c) for at least partial transformation of at least one alcohol obtained from step b) into a mixture of products comprising at least one oxygen-containing compound containing at least one oxygen atom bonded to two distinct carbon atoms which are not bonded together and not comprising a multiple bond in the presence of an acidic dehydration catalyst, which catalyst comprises at least one solid mineral grafted with at least one alkyl sulphonic, aryl sulphonic or arylalkyl sulphonic type organic group.

2. A process according to claim 1, wherein the feed is an olefinic feed.

3. A process according to claim 1, in which hydroformylation step a) is carried out in the presence of a catalyst based on cobalt carbonyl, at a temperature in the range about 100° C. to 200° C., and at a total pressure in the range about 10 to 50 MPa.

4. A process according to claim 2, wherein the olefinic feed is from an FCC unit.

5. A process for preparing an oxygen-containing compound containing at least one oxygen atom bonded to two distinct carbon atoms which are not bonded together and not comprising a multiple bond which is from the acetal group, said process comprising:

a step a) for catalytic hydrofornylation of a feed comprising at least one olefin containing four to seven carbon atoms to at least one aldehyde, a step b) for hydrogenating said aldehyde to at least one corresponding alcohol carried out in the liquid phase in two successive steps, in a first step using a catalyst based on molybdenum disulphide on carbon and in a second step using a catalyst based on nickel on alumina, each of these steps being carried out at a temperature in the range of 100° C. to 300° C. and at a partial pressure of hydrogen in the range of 10 to 30 MPa, and a step c) for at least partial transformation of at least one alcohol obtained from step b) into a mixture of products comprising at least one oxygen-containing compound containing at least one oxygen atom bonded to two distinct carbon atoms which are not bonded together and not comprising a multiple bond in the presence of an $H^+$ ion exchange resin at a temperature range of 70° C. to 100° C., and wherein transformation of the alcohol in step c) yields a mixture of products comprising an acetal having 11 to 17 carbon atoms, unconverted alcohol and water.

6. A process according to claim 5, wherein the feed is an olefinic feed.

7. A process according to claim 6, wherein the olefinic feed is from an FCC unit.

8. A process according to claim 1, in which the mixture obtained from step c) is separated by distillation into a fraction F1 containing ether and unconverted alcohol and into a fraction F2 containing the olefin and water.

9. A process according to claim 8, in which a fraction containing ether and a fraction containing alcohol are separated from fraction F1 by distillation.

10. A process according to claim 8, in which fraction F2 is separated by decanting into a fraction containing the olefin which is recycled to hydroformylation step a), and into an aqueous fraction.

11. A process according to claim 5, in which hydroformylation step a) is carried out in the presence of a catalyst based on cobalt carbonyl, at a temperature in the range about 100° C. to 200° C., and at a total pressure in the range about 10 to MPa.

12. A process according to claim 5, in which acetal synthesis is carried out in the presence of a sulphonic resin, a volume of catalyst per hour (HSV) of about 0.1 to 10 $h^{-1}$, and at a pressure in the range about 0.2 to 1 MPa and with a mole ratio between the 1,3,5-trioxane and the alcohol in the range about 3 to 20.

13. A process according to claim 5, in which the product obtained in step c) is separated into a fraction containing the acetal formed and a fraction containing unconverted alcohol.

14. A process according to claim 5, in which the product obtained in step c) is sent to a first atmospheric pressure distillation zone from which a fraction F3 containing the acetal formed in step c) is obtained and a fraction F4 containing unconverted alcohol is obtained and said fraction F3 is sent to a distillation zone operated at a reduced pressure of between about 100 and 500 Pa from which a fraction F5 containing purified acetal and a residue F6 are recovered.

15. A process according to claim 14, in which the fraction F4 containing a portion of the unconverted alcohol obtained from step c) is sent to a distillation zone from which a fraction F6 containing purified alcohol is recovered and recycled to the acetal formation step c).

* * * * *

UNITED STATES PATENT AND TRADEMARK OFFICE
CERTIFICATE OF CORRECTION

PATENT NO. : 6,486,362 B1 Page 1 of 1
DATED : November 26, 2002
INVENTOR(S) : Alain Forestiere et al.

It is certified that error appears in the above-identified patent and that said Letters Patent is hereby corrected as shown below:

Title page,
Item [75], Inventors, reads "Lyons" should read -- Lyon --
Item [73], Assignee, reads "Rueil Malmaison" should read -- Rueil-Malmaison --

Column 9,
Line 18, reads "catalytic hydrofornylation" should read -- catalytic hydroformylation --

Signed and Sealed this

Twenty-eighth Day of October, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,486,362 B1
DATED : November 26, 2002
INVENTOR(S) : Alain Forestiere et al.

It is certified that error appears in the above-identified patent and that said Letters Patent is hereby corrected as shown below:

<u>Title page,</u>
Item [30], Foreign Application Priority Data, "Jun. 26," should read -- Jun. 29, --

Signed and Sealed this

Sixteenth Day of December, 2003

JAMES E. ROGAN
*Director of the United States Patent and Trademark Office*